United States Patent
Eeckhout et al.

(12) 
(10) Patent No.: US 6,300,336 B1
(45) Date of Patent: Oct. 9, 2001

(54) METHOD OF TREATING OR INHIBITING FUNCTIONAL DISTURBANCES OR ILLNESSES OF THE LOWER INTESTINAL TRACTS, PARTICULARLY ABDOMINAL VISCERAL PAIN WHICH ACCOMPANIES THEM

(75) Inventors: Christian Eeckhout, Lindwedel; Holger Sann, Hannover, both of (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 0 days.

(21) Appl. No.: 09/525,896

(22) Filed: Mar. 15, 2000

(30) Foreign Application Priority Data

Mar. 15, 1999 (DE) .............................. 199 11 371

(51) Int. Cl.$^7$ .................................................. A61K 31/505
(52) U.S. Cl. .............................................................. 514/269
(58) Field of Search ............................................. 514/269

(56) References Cited

U.S. PATENT DOCUMENTS

| 4,323,570 | 4/1982 | Stenzel et al. | 424/251 |
|---|---|---|---|
| 5,712,283 | 1/1998 | Kaan et al. | 514/269 |
| 5,846,974 | * 12/1998 | Kallman et al. | 514/269 |
| 5,914,330 | 6/1999 | Ritz et al. | 514/269 |
| 5,958,934 | * 9/1999 | Berger et al. | 514/272 |
| 5,972,948 | 10/1999 | Kaan et al. | 514/269 |
| 6,054,461 | * 4/2000 | Fairbanks et al. | 514/269 |
| 6,117,879 | * 9/2000 | Fairbanks et al. | 514/269 |

FOREIGN PATENT DOCUMENTS 28 49 537   5/1980   (DE) .

* cited by examiner

*Primary Examiner*—James H. Reamer
(74) *Attorney, Agent, or Firm*—Crowell & Moring LLP

(57) ABSTRACT

The use of moxonidine or a physiologically compatible acid addition salt thereof for the treatment and/or inhibition of functional gastrointestinal disturbances or illnesses in the region of the lower intestinal tracts, particularly for the treatment and/or inhibition of abdominal visceral pain which accompanies them, and the preparation of pharmaceutical compositions suitable for this treatment are is described. The functional disturbances and illnesses of the lower intestinal tracts which can be treated according to the invention are known in particular as irritable bowel syndrome (IBS) and inflammatory bowel disease (IBD), which generally also include visceral pain as one of their symptoms.

4 Claims, No Drawings

METHOD OF TREATING OR INHIBITING FUNCTIONAL DISTURBANCES OR ILLNESSES OF THE LOWER INTESTINAL TRACTS, PARTICULARLY ABDOMINAL VISCERAL PAIN WHICH ACCOMPANIES THEM

BACKGROUND OF THE INVENTION

The present invention relates to the use of 4-chloro-5-[(4,5-dihydro-1H-imidazol-2-yl)-amino]-6-methoxy-2-methylpyrimidine (=moxonidine) and the physiologically compatible acid addition salts thereof for the treatment and/or prophylaxis of functional gastrointestinal disturbances and illnesses in the region of the lower intestinal tracts, in particular for the treatment and/or prophylaxis of abdominal visceral pain which accompanies them, and to the preparation of medicaments suitable for this treatment and/or prophylaxis.

SUMMARY OF THE INVENTION

It is an object of the invention to provide a new method for the treatment of functional and/or illness-related symptoms in the region of the lower intestinal tracts, and in particular, for example, for the treatment and/or inhibition of abdominal visceral pain which accompanies them.

According to the invention, 4-chloro-5-[(4,5-dihydro-1H-imidazol-2-yl)-amino]-6-methoxy-2-methylpyrimidine of the general Formula I

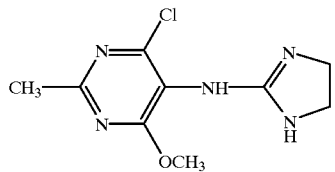

or a physiologically compatible acid addition salt thereof is used for the preparation of pharmaceutical preparations for the treatment and/or inhibition of functional disturbances and illnesses of the lower intestinal tracts which involve increased sensitivity to pain in the colon region, preferably for the treatment and/or prophylaxis of abdominal visceral pain which accompanies them, in larger mammals and humans.

Suitable physiologically compatible acid addition salts of moxonidine include salts with inorganic acids, for example hydrohalic acids, or with organic acids, for example lower aliphatic monocarboxylic or dicarboxylic acids, such as acetic acid, fumaric acid or tartaric acid, or aromatic carboxylic acids such as salicylic acid.

The compounds used according to the invention fall within the scope of 5-[(2-imidazolin-2-yl)-amino]-pyrimidine derivatives having hypotensive properties as described in German Patent Application No. DE 28 49 537, and are known from this patent application. Pharmaceutical preparations which contain moxonidine are commercially available as antihypertensive agents under the trade name Physiotens™, and are medicinally used as antihypertensive agents. The compounds may be prepared in known manner according to the methods described in the above patent application, or analogously to these methods. Moxonidine and its physiologically acceptable salts have also been found to have hyperglycemia inhibiting activity (See U.S. Pat. Nos. 5,972,948 and 5,712,283) and to exert a nephroprotective function (See U.S. Pat. No. 5,914,330).

It has now surprisingly been found that moxonidine and its physiologically compatible acid addition salts not only are suitable for the treatment of illnesses of the cardiovascular system, such as in particular for the treatment of hypertension, as stated in the German patent application cited above, but also can be used for the treatment and/or prophylaxis of functional disturbances and illnesses of the lower intestinal tracts. Moxonidine and the physiologically compatible acid addition salts thereof are suitable in particular for the treatment and/or prophylaxis of abdominal visceral pain which accompanies these functional disturbances and illnesses.

The functional disturbances which can be treated by the compounds used according to the invention therefore include in particular the disturbances of the lower intestinal tracts which are called "irritable bowel syndrome" (=IBS). The essential symptoms of IBS are pain in the lower abdomen, which is considerably jointly caused by hypersensitivity of the visceral afferent nervous system. The increased visceral sensitivity to pain with respect to mechanical or chemical stimuli in the intestinal tract results in IBS patients suffering severe visceral pain even with only physiological slight distension of the colon owing to digestion, e.g. even with only slight gas formation and slight flatulence, which are scarcely noticed by healthy individuals. The symptoms observed what is called "irritable bowel syndrome" (=IBS) include, in addition to motility disturbances in the lower intestinal region and disturbances of stool passage, such as in particular abnormally accelerated passage of the stool in the colon, and therefore to a particular extent also visceral pain. The compounds used according to the invention in this case have a beneficial action with marked action components with respect to visceral pain in the colon.

Disturbances in the gastrointestinal tract may also be caused by inflammatory diseases, such as diseases like those grouped under the term "inflammatory bowel disease" (IBD), which may likewise involve increased visceral sensitivity to pain.

It has now been discovered that moxonidine and its pharmacologically acceptable acid addition salts reduce visceral sensitivity to pain. Owing to their beneficial action on abdominal visceral sensitivity to pain, moxonidine and its pharmacologically acceptable acid addition salts are therefore suitable in particular for the treatment and/or prophylaxis of abdominal visceral pain, such as may occur in particular in conjunction with IBS or IBD.

Moxonidine and its physiologically compatible acid addition salts may be administered in conventional pharmaceutical preparations, orally, intravenously or alternatively transdermally for the treatment according to the invention of illnesses and functional disturbances and illnesses of the lower intestinal tracts, in particular for example for the treatment and/or prophylaxis of visceral pain which accompanies them.

Thus moxonidine and its physiologically compatible acid addition salts may be contained, together with conventional pharmaceutical auxiliaries and/or carriers, in solid or liquid pharmaceutical preparations, in a quantity effective for the treatment of functional disturbances and illnesses of the lower intestinal tracts, in particular, for example, in a quantity effective for the treatment and/or inhibition of visceral pain which accompanies them. Examples of solid preparations which may be formulated for the direct or delayed release of active substance include preparations which can be administered orally, such as tablets, coated tablets, capsules, powders or granules, or alternatively suppositories and plasters (transdermal therapeutic systems). These solid preparations may contain conventional pharmaceutical inorganic and/or organic carriers, such as lactose, talcum or starch, in addition to conventional pharmaceutical auxiliaries, for example lubricants or tablet disintegrating agents. In the case of plasters, the active substance is kept in an active-substance reservoir, in particular, for example, an active-substance matrix (e.g. a polymer matrix). Liquid preparations such as solutions, suspensions or emulsions of the active substances may contain the usual diluents such as water, oils and/or suspension agents such as polyethylene glycols and the like. Other auxiliaries may additionally be added, such as preservatives, taste correctives and the like.

The active substances may be mixed and formulated with the pharmaceutical auxiliaries and/or carriers in known manner. For the production of solid medicament forms, the active substances may for example be mixed with the auxiliaries and/or carriers in conventional manner and may be granulated in the wet or dry state. The granules or powder may be poured directly into capsules or be pressed into tablet cores in conventional manner. These may be coated in known manner if desired. Plasters or transdermal therapeutic systems may be constructed in the conventional manner e.g. from a covering film, active-substance reservoir (self-adhesive or with additional adhesive layer) and tear-off film and as matrix-controlled or membrane-controlled systems (i.e. equipped with an additional control membrane).

The pharmacological activity of moxonidine and its pharmacologically acceptable acid addition salts in the region of the lower intestinal tracts can be demonstrated in standard pharmacological tests on animals.

DESCRIPTION OF THE PHARMACOLOGICAL TEST METHODS

Investigation of the action of the compounds on visceral sensitivity to pain in rats.

Visceral pain leads to visceral reactions which manifest themselves, inter alia, by contractions of the abdominal muscles. The number of contractions of the abdominal muscles occurring after a mechanical pain stimulus produced by distending the large intestine is thus a measurement for determining the visceral sensitivity to pain.

The inhibiting action of the test substances on distension-induced abdominal contractions was tested on rats. The distension of the large intestine with an introduced balloon was used as the stimulus; the contraction of the abdominal muscles was measured as response. One hour after the sensitising of the large intestine by instillation of dilute acetic acid (0.6%, 1.5 ml), a latex balloon was introduced and inflated to 100 mbar for 10 minutes. During this time, the contractions of the abdominal muscles were counted. 20 minutes after subcutaneous administration of the test substance, this measurement was repeated. The action of the test substance was calculated as a percentage reduction in the counted contractions compared with the control. The reductions in the number of abdominal contractions achieved with different doses of the test substance moxonidine are listed in percentages, relative to the control values (=100%) measured before ingestion of the substance in the following Table 1.

TABLE 1

Influence on Visceral Sensitivity

| Dose of the test substance moxonidine | Reduction in the number of distension-induced contractions of the abdominal muscles in % relative to control value = 100% |
|---|---|
| 0.3 mg/kg | approx. 9% (already slight action) |
| 0.6 mg/kg | 23% |
| 1.0 mg/kg | 57% |
| 1.5 mg/kg | 71% |

The reduction, achieved by the test substance moxonidine, in the number of abdominal contractions induced by distension stimulus is a clear indicator of the effectiveness of the test substances with respect to visceral sensitivity to pain.

The foregoing test results therefore show that moxonidine and the pharmacologically acceptable acid addition salts thereof are capable of reducing visceral sensitivity to pain, and consequently are suitable for the treatment and/or inhibition of visceral pain in the region of the lower intestinal tracts. The aforementioned compounds can therefore be advantageously used for the treatment and/or inhibition of functional disturbances and illnesses of the lower intestinal tracts which are generally accompanied by visceral pain, such as in particular IBS or IBD.

The doses to be used may vary individually and will naturally vary according to the type of condition to be treated and the form of administration. In general, the daily doses for the treatment of functional disturbances and/or illnesses of the lower intestinal tracts, in particular for example for the treatment and/or prophylaxis of visceral pain which accompanies them in humans, for oral administration are in the range of 0.05 to 5 mg, preferably about 0.25 to 3 mg. Moxonidine or its acid addition salts may in this case be administered in pharmaceutical preparations both for immediate and for delayed and controlled release of active substance. In this case, it will be automatically understood by persons skilled in the art that preparations with delayed and controlled release of active substance may have higher contents of active substance than preparations for immediate release of active substance.

The following example is intended to illustrate the preparation of a pharmaceutical preparation containing moxonidine or a pharmaceutically acceptable acid addition salt thereof in greater detail, but without restricting the scope of the invention.

EXAMPLE 1

Film-coated Tablets Containing Moxonidine
  Composition:

| Tablet cores: | | |
|---|---|---|
| Moxonidine | 0.025 | parts |
| Lactose | 9.575 | parts |
| Povidone USP | 0.070 | parts |
| Crospovidone USP | 0.300 | parts |
| Magnesium stearate | 0.030 | parts |
| (Water | 0.750 | parts) |
| Total Solids | 10.000 | parts |
| Film coating: | | |
| Hydroxypropylmethylcellulose | 0.156 | parts |
| 30% aqueous ethylcellulose dispersion | 0.480 | parts |

| | | |
|---|---|---|
| -continued | | |
| (=solid) | (0.144) | parts |
| Polyethylene glycol 6000 | 0.030 | parts |
| Titanium dioxide | 0.150 | parts |
| Talc | 0.1197 | parts |
| Red iron oxide | 0.0003 | parts |
| (Water | 3.864 | parts) |
| Total solids | 0.600 | parts |
| Total quantity of film coating suspension | 4.800 | parts |

4.8 kg of the above film coating suspension were used for coating 10,000 tablet cores each of 100 mg in weight.

Production of Tablet Cores

The moxonidine and the lactose were mixed. The mixture was thoroughly moistened with a solution of the binder, Povidone, in water, was thoroughly kneaded, and the resulting product was spread on trays and dried at a temperature of about 50° C. to a moisture content of at most 0.5%. The dried product was passed through a 0.75 mm sieve (Frewitt machine). After the resulting granules had been mixed with Crospovidone and magnesium stearate, tablet cores weighing 100 mg each were pressed therefrom, so that each tablet core contained 0.25 mg of the active substance.

Production of the Film Coating Suspension

The hydroxypropylmethylcellulose and the polyethylene glycol 6000 were dissolved in a portion of the water. A suspension of talc, titanium dioxide and iron oxide in the rest of the water was added to this solution with stirring. The resulting suspension was diluted with the 30% aqueous ethylcellulose dispersion with light stirring.

Film Coating of the Tablet Cores

The film coating suspension was sprayed onto the tablet cores in a film-coating apparatus, while hot air at approximately 70° C. heated the tablet cores to a temperature of approximately 45° C. Then the film coated tablets were dried for 16 hours at a temperature of approximately 45° C.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A method of treating or inhibiting irritable bowel syndrome, in a mammal, said method comprising administering to said mammal an effective amount of the compound 4-chloro-5-[(4,5-dihydro-1H-imidazol-2-yl)-amino]-6-methoxy-2-methylpyrimidine corresponding to the formula I

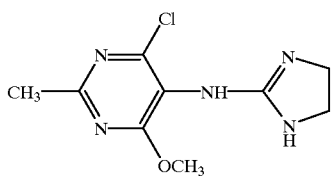

or a physiologically acceptable salt thereof.

2. A method according to claim 1, wherein said compound is orally administered.

3. A method according to claim 1, wherein said compound is administered in conjunction with at least one pharmaceutical carrier or auxiliary agent.

4. A method according to claim 1, wherein said compound is orally administered in the form of a film-coated tablet.

* * * * *